(12) United States Patent
Errico et al.

(10) Patent No.: US 7,711,430 B2
(45) Date of Patent: *May 4, 2010

(54) METHODS AND APPARATUS FOR TREATING ANAPHYLAXIS USING ELECTRICAL MODULATION

(75) Inventors: Joseph P. Errico, Green Brook, NJ (US); Steven Mendez, Chester, NJ (US)

(73) Assignee: ElectroCore LLC, Morris Plains, NJ (US)

( * ) Notice: Subject to any disclaimer, the term of this patent is extended or adjusted under 35 U.S.C. 154(b) by 516 days.

This patent is subject to a terminal disclaimer.

(21) Appl. No.: 11/591,768

(22) Filed: Nov. 2, 2006

(65) Prior Publication Data

US 2007/0191902 A1    Aug. 16, 2007

Related U.S. Application Data

(60) Provisional application No. 60/772,361, filed on Feb. 10, 2006.

(51) Int. Cl.
*A61N 1/00* (2006.01)
(52) U.S. Cl. ...................................... 607/42
(58) Field of Classification Search .............. 607/2–3, 607/42, 96
See application file for complete search history.

(56) References Cited

U.S. PATENT DOCUMENTS

| | | | |
|---|---|---|---|
| 3,946,745 A | 3/1976 | Hsiang-Lai et al. |
| 3,949,743 A | 4/1976 | Shanbrom |
| 4,305,402 A | 12/1981 | Katims |
| 4,351,330 A | 9/1982 | Scarberry |
| 4,503,863 A | 3/1985 | Katims |
| 4,649,935 A | 3/1987 | Charmillot et al. |
| 4,765,322 A | 8/1988 | Charmillot et al. |
| 4,904,472 A | 2/1990 | Belardinelli et al. |
| 4,945,910 A | 8/1990 | Budyko et al. |
| 4,989,604 A | 2/1991 | Fang |
| 5,054,486 A | 10/1991 | Yamada |
| 5,107,835 A | 4/1992 | Thomas |
| 5,109,846 A | 5/1992 | Thomas |
| 5,123,413 A | 6/1992 | Hasegawa |
| 5,135,480 A | 8/1992 | Bannon et al. |
| 5,152,286 A | 10/1992 | Sitko et al. |

(Continued)

FOREIGN PATENT DOCUMENTS

WO    9301862    2/1993

(Continued)

OTHER PUBLICATIONS

International Search Report and Written Opinion for corresponding application PCT/US2006/42752.

(Continued)

*Primary Examiner*—George Manuel
*Assistant Examiner*—Robert N Wieland
(74) *Attorney, Agent, or Firm*—John T. Raffle

(57) ABSTRACT

Methods and devices for treating anaphylaxis, anaphylactic shock, bronchial constriction, and/or asthma include providing an electrical impulse to a selected region of the vagus nerve of a patient suffering from anaphylaxis to block and/or modulate nerve signals that would regulate the function of, for example, myocardial tissue, vasodilation/constriction and/or pulmonary tissue.

32 Claims, 6 Drawing Sheets

U.S. PATENT DOCUMENTS

| | | | |
|---|---|---|---|
| 5,263,480 A | 11/1993 | Wernicke et al. | |
| 5,405,362 A | 4/1995 | Kramer et al. | |
| 5,405,366 A | 4/1995 | Fox et al. | |
| 5,437,291 A | 8/1995 | Pasricha et al. | |
| 5,454,840 A | 10/1995 | Krakovsky et al. | |
| 5,540,730 A | 7/1996 | Terry, Jr. et al. | |
| 5,620,463 A | 4/1997 | Drolet | |
| 5,658,322 A | 8/1997 | Fleming | |
| 5,674,205 A | 10/1997 | Pasricha et al. | |
| 5,690,692 A | 11/1997 | Fleming | |
| 5,707,400 A | 1/1998 | Terry, Jr. et al. | |
| 5,814,078 A | 9/1998 | Zhou et al. | |
| 5,849,026 A | 12/1998 | Zhou | |
| 5,861,014 A | 1/1999 | Familoni | |
| 5,891,182 A | 4/1999 | Fleming | |
| 5,911,218 A | 6/1999 | DiMarco | |
| 5,931,806 A | 8/1999 | Shimada | |
| 5,956,501 A | 9/1999 | Brown | |
| 5,972,026 A | 10/1999 | Laufer et al. | |
| 5,995,873 A | 11/1999 | Rhodes | |
| 6,006,134 A | 12/1999 | Hill et al. | |
| 6,043,273 A | 3/2000 | Duhaylongsod | |
| 6,060,454 A | 5/2000 | Duhaylongsod | |
| 6,083,249 A | 7/2000 | Familoni | |
| 6,083,255 A | 7/2000 | Laufer et al. | |
| 6,087,394 A | 7/2000 | Duhaylongsod | |
| 6,101,412 A | 8/2000 | Duhaylongsod | |
| 6,125,301 A | 9/2000 | Capel | |
| 6,127,410 A | 10/2000 | Duhaylongsod | |
| 6,141,589 A | 10/2000 | Duhaylongsod | |
| 6,198,970 B1 | 3/2001 | Freed et al. | |
| 6,200,333 B1 | 3/2001 | Laufer | |
| 6,203,562 B1 | 3/2001 | Ohkubo | |
| 6,212,432 B1 | 4/2001 | Matsuura | |
| 6,230,052 B1 | 5/2001 | Wolff et al. | |
| 6,258,087 B1 | 7/2001 | Edwards | |
| 6,273,886 B1 | 8/2001 | Edwards et al. | |
| 6,273,907 B1 | 8/2001 | Laufer | |
| 6,283,988 B1 | 9/2001 | Laufer | |
| 6,283,989 B1 | 9/2001 | Laufer | |
| 6,299,633 B1 | 10/2001 | Laufer | |
| 6,325,798 B1 | 12/2001 | Edwards et al. | |
| 6,327,503 B1 | 12/2001 | Familoni | |
| 6,341,236 B1 | 1/2002 | Osorio et al. | |
| 6,342,221 B1 | 1/2002 | Thorpe et al. | |
| 6,356,786 B1 | 3/2002 | Rezai et al. | |
| 6,356,787 B1 | 3/2002 | Rezai et al. | |
| 6,363,937 B1 | 4/2002 | Hovda | |
| 6,366,814 B1 | 4/2002 | Boveja et al. | |
| 6,402,744 B2 | 6/2002 | Edwards | |
| 6,411,852 B1 | 6/2002 | Danek et al. | |
| 6,414,018 B1 | 7/2002 | Duhaylongsod | |
| 6,423,058 B1 | 7/2002 | Edwards | |
| 6,424,864 B1 | 7/2002 | Matsuura | |
| 6,438,423 B1 | 8/2002 | Rezai et al. | |
| 6,440,128 B1 | 8/2002 | Edwards et al. | |
| 6,464,697 B1 | 10/2002 | Edwards et al. | |
| 6,485,416 B1 | 11/2002 | Platt et al. | |
| 6,547,776 B1 | 4/2003 | Gaiser et al. | |
| 6,549,808 B1 | 4/2003 | Gisel et al. | |
| 6,562,034 B2 | 5/2003 | Edwards et al. | |
| 6,587,719 B1 | 7/2003 | Barrett et al. | |
| 6,609,030 B1 | 8/2003 | Rezai | |
| 6,610,713 B2 | 8/2003 | Tracey | |
| 6,629,951 B2 | 10/2003 | Laufer et al. | |
| 6,633,779 B1 | 10/2003 | Schuler et al. | |
| 6,656,960 B2 | 12/2003 | Puskas | |
| 6,675,047 B1 | 1/2004 | Konoplev et al. | |
| 6,676,686 B2 | 1/2004 | Naganuma | |
| 6,681,136 B2 | 1/2004 | Schuler et al. | |
| 6,711,436 B1 | 3/2004 | Duhaylongsod | |
| 6,712,074 B2 | 3/2004 | Edwards | |
| 6,738,667 B2 | 5/2004 | Deno et al. | |
| 6,752,765 B1 | 6/2004 | Strobel et al. | |
| 6,755,849 B1 | 6/2004 | Gowda et al. | |
| 6,778,854 B2 | 8/2004 | Puskas | |
| 6,819,956 B2 | 11/2004 | DiLorenzo | |
| 6,838,429 B2 | 1/2005 | Paslin | |
| 6,853,862 B1 | 2/2005 | Marchal et al. | |
| 6,871,092 B2 | 3/2005 | Piccone | |
| 6,871,099 B1 | 3/2005 | Whitehurst et al. | |
| 6,872,206 B2 | 3/2005 | Edwards | |
| 6,876,885 B2 | 4/2005 | Swoyer et al. | |
| 6,885,888 B2 | 4/2005 | Rezai | |
| 6,913,616 B2 | 7/2005 | Hamilton et al. | |
| 6,934,583 B2 | 8/2005 | Weinberg et al. | |
| 6,937,896 B1 | 8/2005 | Kroll | |
| 6,937,903 B2 | 8/2005 | Schuler et al. | |
| 6,957,106 B2 | 10/2005 | Schuler et al. | |
| 6,961,622 B2 | 11/2005 | Gilbert | |
| 6,970,742 B2 | 11/2005 | Mann et al. | |
| 6,974,224 B2 | 12/2005 | Thomas-Benedict | |
| 7,142,910 B2 | 11/2006 | Puskas | |
| 7,292,890 B2 | 11/2007 | Whitehurst et al. | |
| 7,310,552 B2 | 12/2007 | Puskas | |
| 7,363,076 B2 * | 4/2008 | Yun et al. | 607/3 |
| 7,594,925 B2 * | 9/2009 | Danek et al. | 607/96 |
| 2002/0002387 A1 | 1/2002 | Naganuma | |
| 2002/0010495 A1 | 1/2002 | Freed et al. | |
| 2002/0016344 A1 | 2/2002 | Tracey | |
| 2002/0072738 A1 | 6/2002 | Edwards | |
| 2002/0091379 A1 | 7/2002 | Danek et al. | |
| 2002/0107515 A1 | 8/2002 | Edwards et al. | |
| 2002/0111386 A1 | 8/2002 | Sekins et al. | |
| 2002/0116030 A1 | 8/2002 | Rezai | |
| 2002/0143373 A1 | 10/2002 | Courtnage et al. | |
| 2002/0151888 A1 | 10/2002 | Edwards | |
| 2002/0183682 A1 | 12/2002 | Darvish | |
| 2002/0198570 A1 | 12/2002 | Puskas | |
| 2002/0198574 A1 | 12/2002 | Gumpert | |
| 2003/0023287 A1 | 1/2003 | Edwards et al. | |
| 2003/0074039 A1 | 4/2003 | Puskas | |
| 2003/0093128 A1 | 5/2003 | Freed et al. | |
| 2003/0144572 A1 | 7/2003 | Oschman et al. | |
| 2003/0181949 A1 | 9/2003 | Whale | |
| 2003/0216791 A1 | 11/2003 | Schuler et al. | |
| 2003/0216792 A1 | 11/2003 | Levin et al. | |
| 2003/0233099 A1 | 12/2003 | Danaek et al. | |
| 2004/0010289 A1 | 1/2004 | Biggs et al. | |
| 2004/0029849 A1 | 2/2004 | Schatzberg et al. | |
| 2004/0030368 A1 | 2/2004 | Kemeny et al. | |
| 2004/0044390 A1 | 3/2004 | Szeles | |
| 2004/0059383 A1 | 3/2004 | Puskas | |
| 2004/0073278 A1 | 4/2004 | Pachys | |
| 2004/0088030 A1 | 5/2004 | Jung, Jr. | |
| 2004/0088036 A1 | 5/2004 | Gilbert | |
| 2004/0106954 A1 | 6/2004 | Whitehurst et al. | |
| 2004/0116981 A1 | 6/2004 | Mazar | |
| 2004/0122488 A1 | 6/2004 | Mazar et al. | |
| 2004/0122489 A1 | 6/2004 | Mazar et al. | |
| 2004/0127942 A1 | 7/2004 | Yomtov et al. | |
| 2004/0127953 A1 | 7/2004 | Kilgore et al. | |
| 2004/0127958 A1 | 7/2004 | Mazar et al. | |
| 2004/0147969 A1 | 7/2004 | Mann et al. | |
| 2004/0147988 A1 | 7/2004 | Stephens | |
| 2004/0162597 A1 | 8/2004 | Hamilton et al. | |
| 2004/0167580 A1 | 8/2004 | Mann et al. | |
| 2004/0172075 A1 | 9/2004 | Shafer et al. | |
| 2004/0172080 A1 | 9/2004 | Stadler et al. | |
| 2004/0172084 A1 | 9/2004 | Knudson et al. | |
| 2004/0176803 A1 | 9/2004 | Whelan et al. | |
| 2004/0176805 A1 | 9/2004 | Whelan et al. | |
| 2004/0204747 A1 | 10/2004 | Kemeny et al. | |
| 2004/0215289 A1 | 10/2004 | Fukui | |

| | | |
|---|---|---|
| 2004/0220621 A1 | 11/2004 | Zhou et al. |
| 2004/0230251 A1 | 11/2004 | Schuler et al. |
| 2004/0230252 A1 | 11/2004 | Kullok et al. |
| 2004/0243182 A1 | 12/2004 | Cohen |
| 2004/0249416 A1 | 12/2004 | Yun et al. |
| 2005/0004609 A1 | 1/2005 | Stahmann et al. |
| 2005/0004631 A1 | 1/2005 | Benedict |
| 2005/0010263 A1 | 1/2005 | Schauerte |
| 2005/0010270 A1 | 1/2005 | Laufer |
| 2005/0015117 A1 | 1/2005 | Gerber |
| 2005/0021092 A1 | 1/2005 | Yun et al. |
| 2005/0059153 A1 | 3/2005 | George et al. |
| 2005/0065553 A1 | 3/2005 | Ben Ezra et al. |
| 2005/0065562 A1 | 3/2005 | Rezai |
| 2005/0065567 A1 | 3/2005 | Lee et al. |
| 2005/0065573 A1 | 3/2005 | Rezai |
| 2005/0065574 A1 | 3/2005 | Rezai |
| 2005/0075701 A1 | 4/2005 | Shafer |
| 2005/0075702 A1 | 4/2005 | Shafer |
| 2005/0076909 A1 | 4/2005 | Stahmann et al. |
| 2005/0080461 A1 | 4/2005 | Stahmann et al. |
| 2005/0090722 A1 | 4/2005 | Perez |
| 2005/0107829 A1 | 5/2005 | Edwards |
| 2005/0125044 A1 | 6/2005 | Tracey |
| 2005/0143788 A1 | 6/2005 | Yun et al. |
| 2005/0149146 A1 | 7/2005 | Boveja et al. |
| 2005/0153885 A1 | 7/2005 | Yun et al. |
| 2005/0159736 A9 | 7/2005 | Danek et al. |
| 2005/0165456 A1 | 7/2005 | Mann et al. |
| 2005/0177192 A1 | 8/2005 | Rezai et al. |
| 2005/0182288 A1 | 8/2005 | Zabara |
| 2005/0187579 A1 | 8/2005 | Danek et al. |
| 2005/0216062 A1 | 9/2005 | Herbst |
| 2005/0222628 A1 | 10/2005 | Krakousky |
| 2005/0222635 A1 | 10/2005 | Krakovsky |
| 2005/0222651 A1 | 10/2005 | Jung |
| 2005/0228054 A1 | 10/2005 | Tatton |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0238693 A1 | 10/2005 | Whyte |
| 2005/0240241 A1 | 10/2005 | Yun et al. |
| 2005/0245992 A1 | 11/2005 | Persen et al. |
| 2005/0251213 A1 | 11/2005 | Freeman |
| 2005/0256028 A1 | 11/2005 | Yun et al. |
| 2005/0261747 A1 | 11/2005 | Schuler et al. |
| 2005/0267536 A1 | 12/2005 | Freeman et al. |
| 2005/0277993 A1 | 12/2005 | Mower |
| 2005/0283197 A1 | 12/2005 | Daum et al. |
| 2006/0100666 A1 | 5/2006 | Wilkinson |
| 2006/0135998 A1* | 6/2006 | Libbus et al. ............ 607/2 |
| 2006/0167498 A1 | 7/2006 | DiLorenzo |
| 2006/0178703 A1 | 8/2006 | Huston |
| 2006/0247683 A1 | 11/2006 | Denek |
| 2006/0259028 A1 | 11/2006 | Utley |
| 2006/0259029 A1 | 11/2006 | Utley |
| 2006/0259030 A1 | 11/2006 | Utley |
| 2006/0287679 A1 | 12/2006 | Stone |
| 2007/0027496 A1 | 2/2007 | Parnis et al. |
| 2007/0060954 A1 | 3/2007 | Cameron |
| 2007/0106337 A1 | 5/2007 | Errico |
| 2007/0106338 A1 | 5/2007 | Errico |
| 2007/0106339 A1 | 5/2007 | Errico et al. |
| 2007/0191902 A1 | 8/2007 | Errico et al. |
| 2007/0225768 A1 | 9/2007 | Dobak, III |
| 2008/0183248 A1 | 7/2008 | Rezai et al. |

FOREIGN PATENT DOCUMENTS

| | | |
|---|---|---|
| WO | WO 01/89526 A1 | 11/2001 |
| WO | WO 2004/078252 A2 | 9/2004 |

OTHER PUBLICATIONS

International Preliminary Report on Patentability for corresponding patent PCT/US2006/042823, dated Aug. 21, 2008.

International Search Report and Written Opinion for PCT application PCT/US2009/038081, Jun. 1, 2009.

International Search Report and Written Opinion of the International Searching Authority dated May 20, 2009 of International Application No. PCT/US2009/038081, International filing date Mar. 24, 2009.

International Search Report and Written Opinion of the International Searching Authority dated Jun. 2, 2007 of International Application No. PCT/US06/42828, International filing date Nov. 2, 2006.

Guarini et al., "Efferent Vagal Fibre Stimulation Blunts Nuclear Factor-kB Activation and Protects Against Hypovolemic Hemorrhagic Shock", *Circulation* 2003 vol. 107 pp. 1189-1194.

Supplemental European Search Report for EP Application No. 06827343, Aug. 21, 2009.

Supplemental European Search Report for EP Application No. 06827386.1, Aug. 21, 2009.

U.S. Appl. No. 60/206,364, Title: Vagus Nerve Stimulation Attenuation of the Systemic Inflammatory Response to Endotoxin, Filing Date: May 23, 2000, Inventor: Tracey.

* cited by examiner

METHODS AND APPARATUS FOR TREATING ANAPHYLAXIS USING ELECTRICAL MODULATION

CROSS REFERENCE TO RELATED APPLICATIONS

This application claims the benefit of U.S. Provisional Patent Application No. 60/772,361, filed Feb. 10, 2006, the entire disclosure of which is hereby incorporated by reference.

BACKGROUND OF THE INVENTION

The present invention relates to the field of delivery of electrical impulses to bodily tissues for therapeutic purposes, and more specifically to devices and methods for treating conditions associated with shock, such as anaphylaxis by blocking and/or modulating signals in the vagus nerve.

There are a number of treatments for various infirmities that require the destruction of otherwise healthy tissue in order to affect a beneficial effect. Malfunctioning tissue is identified, and then lesioned or otherwise compromised in order to affect a beneficial outcome, rather than attempting to repair the tissue to its normal functionality. While there are a variety of different techniques and mechanisms that have been designed to focus lesioning directly onto the target nerve tissue, collateral damage is inevitable.

Still other treatments for malfunctioning tissue can be medicinal in nature, in many cases leaving patients to become dependent upon artificially synthesized chemicals. Examples of this are anti-asthma drugs such as albuterol, proton pump inhibitors such as omeprazole (Prilosec), spastic bladder relievers such as Ditropan, and cholesterol reducing drugs like Lipitor and Zocor. In many cases, these medicinal approaches have side effects that are either unknown or quite significant, for example, at least one popular diet pill of the late 1990's was subsequently found to cause heart attacks and strokes.

Unfortunately, the beneficial outcomes of surgery and medicines are, therefore, often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue, which stimulation is generally a wholly reversible and non-destructive treatment, holds significant promise for the treatment of many ailments.

Electrical stimulation of the brain with implanted electrodes has been approved for use in the treatment of various conditions, including pain and movement disorders including essential tremor and Parkinson's disease. The principle behind these approaches involves disruption and modulation of hyperactive neuronal circuit transmission at specific sites in the brain. As compared with the very dangerous lesioning procedures in which the portions of the brain that are behaving pathologically are physically destroyed, electrical stimulation is achieved by implanting electrodes at these sites to, first sense aberrant electrical signals and then to send electrical pulses to locally disrupt the pathological neuronal transmission, driving it back into the normal range of activity. These electrical stimulation procedures, while invasive, are generally conducted with the patient conscious and a participant in the surgery.

Brain stimulation, and deep brain stimulation in particular, is not without some drawbacks. The procedure requires penetrating the skull, and inserting an electrode into the brain matter using a catheter-shaped lead, or the like. While monitoring the patient's condition (such as tremor activity, etc.), the position of the electrode is adjusted to achieve significant therapeutic potential. Next, adjustments are made to the electrical stimulus signals, such as frequency, periodicity, voltage, current, etc., again to achieve therapeutic results. The electrode is then permanently implanted and wires are directed from the electrode to the site of a surgically implanted pacemaker. The pacemaker provides the electrical stimulus signals to the electrode to maintain the therapeutic effect. While the therapeutic results of deep brain stimulation are promising, there are significant complications that arise from the implantation procedure, including stroke induced by damage to surrounding tissues and the neurovasculature.

One of the most successful modern applications of this basic understanding of the relationship between muscle and nerves is the cardiac pacemaker. Although its roots extend back into the 1800's, it was not until 1950 that the first practical, albeit external and bulky pacemaker was developed. Dr. Rune Elqvist developed the first truly functional, wearable pacemaker in 1957. Shortly thereafter, in 1960, the first fully implanted pacemaker was developed.

Around this time, it was also found that the electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to Deno, et al., the disclosure of which is incorporated herein by reference).

Anaphylaxis is a severe allergic reaction that occurs when the body is exposed to a substance to which it was previously sensitized. The reaction causes a sudden release of chemicals, including histamines, from cells in the body's tissues. These chemicals dilate the blood vessels, lowering blood pressure, and cause the blood vessels to leak fluid. The chemicals also act on the lungs, causing the airways to constrict which makes breathing very difficult.

In some cases, anaphylaxis is mild, causing only hives and itching; however, anaphylaxis can be deadly. In anaphylactic shock, the most severe form of anaphylaxis, blood pressure drops severely and bronchial tissues swell dramatically. This causes the person to choke and collapse. Anaphylactic shock is fatal if not treated immediately and causes more than eight thousand deaths per year in the United States alone. The triggers for these fatal reactions range from exposure to nuts, insect stings, medication, etc. However, the triggers are mediated by a series of hypersensitivity responses that result in uncontrollable drop in blood pressure and airway occlusion driven by smooth muscle constriction.

Given the common mediators of both asthmatic and anaphylactic bronchoconstriction, it is not surprising that asthma sufferers are at a particular risk for anaphylaxis. Still, estimates place the numbers of people who are susceptible to such responses at more than 40 million in the United States alone. Tragically, many of these patients are fully aware of the severity of their condition, and die while struggling in vain to manage the attack medically. Many of these incidents occur in hospitals or in ambulances, in the presence of highly trained medical personnel who are powerless to break the cycle of hypotension and bronchoconstriction affecting their patient. Typically, the severity and rapid onset of anaphylactic reactions does not render the pathology to chronic treatment, but requires more immediately acting medications. Among the most popular medications for treating anaphylaxis is epinephrine, commonly marketed in so-called "Epi-pen" formulations and administering devices, which potential sufferers carry with them at all times. In addition to serving as an extreme bronchodilator, epinephrine raises the patient's heart rate dramatically, and can result in tachycardia and heart attacks.

The smooth muscles that line the bronchial passages are controlled by a confluence of vagus and sympathetic nerve fiber plexuses. Spasms of the bronchi during asthma attacks and anaphylactic shock can often be directly related to pathological signaling within these plexuses. Anaphylactic shock and asthma are major health concerns.

Asthma, and other airway occluding disorders resulting from inflammatory responses and inflammation-mediated bronchoconstriction, affects an estimated eight to thirteen million adults and children in the United States. A significant subclass of asthmatics suffers from severe asthma. An estimated 5,000 persons die every year in the United States as a result of asthma attacks. Up to twenty percent of the populations of some countries are affected by asthma, estimated at more than a hundred million people worldwide. Asthma's associated morbidity and mortality are rising in most countries despite increasing use of anti-asthma drugs.

Asthma is characterized as a chronic inflammatory condition of the airways. Typical symptoms are coughing, wheezing, tightness of the chest and shortness of breath. Asthma is a result of increased sensitivity to foreign bodies such as pollen, dust mites and cigarette smoke. The body, in effect, overreacts to the presence of these foreign bodies in the airways. As part of the asthmatic reaction, an increase in mucous production is often triggered, exacerbating airway restriction. Smooth muscle surrounding the airways goes into spasm, resulting in constriction of airways. The airways also become inflamed. Over time, this inflammation can lead to scarring of the airways and a further reduction in airflow. This inflammation leads to the airways becoming more irritable, which may cause an increase in coughing and increased susceptibility to asthma episodes.

Two medicinal strategies exist for treating this problem for patients with asthma. The condition is typically managed by means of inhaled medications that are taken after the onset of symptoms, or by injected and/or oral medication that are taken chronically. The medications typically fall into two categories; those that treat the inflammation, and those that treat the smooth muscle constriction. The first is to provide anti-inflammatory medications, like steroids, to treat the airway tissue, reducing its tendency to over-release of the molecules that mediate the inflammatory process. The second strategy is to provide a smooth muscle relaxant (an anticholinergic and/or anti-adrenergic medication) to reduce the ability of the muscles to constrict.

It has been highly preferred that patients rely on avoidance of triggers and anti-inflammatory medications, rather than on the bronchodilators as their first line of treatment. For some patients, however, these medications, and even the bronchodilators are insufficient to stop the constriction of their bronchial passages, and more than five thousand people suffocate and die every year as a result of asthma attacks.

Myocardial dysfunction involves a decrease in overall myocardial performance. The determinants of myocardial performance are heart rate, preload, afterload, and contractility. Heart rate is a term used to describe the frequency of the cardiac cycle, usually in number of number of contractions of the heart (heart beats) per minute. The heart contains two natural cardiac pacemakers that spontaneously cause the heart to beat. These can be controlled by the autonomic nervous system and circulating adrenaline.

The body can increase the heart rate in response to a wide variety of conditions in order to increase the cardiac output (the amount of blood ejected by the heart per unit time). Exercise, environmental stressors or psychological stress can cause the heart rate to increase above the resting rate. The pulse is the most straightforward way of measuring the heart rate, but it can be deceptive when some strokes do not lead to much cardiac output. In these cases (as happens in some arrhythmias), the heart rate may be considerably higher than the pulse.

Preload is theoretically most accurately described as the initial stretching of cardiac myocytes prior to contraction. Preload is the volume of blood present in a ventricle of the heart, after passive filling and atrial contraction. Preload is affected by venous blood pressure and the rate of venous return. These are affected by venous tone and volume of circulating blood.

Afterload is the tension produced by a chamber of the heart in order to contract. Afterload can also be described as the pressure that the chamber of the heart has to generate in order to eject blood out of the chamber. In the case of the left ventricle, the afterload is a consequence of the blood pressure, since the pressure in the ventricle must be greater than the blood pressure in order to open the aortic valve. For instance, hypertension (increased blood pressure) increases the left ventricular afterload because the left ventricle has to work harder to eject blood into the aorta. This is because the aortic valve won't open until the pressure generated in the left ventricle is higher than the elevated blood pressure.

Contractility is the intrinsic ability of a cardiac muscle fiber to contract at any given fiber length. If myocardial performance changes while preload, afterload and heart rate are all constant, then the change in performance must be due to the change in contractility. Chemicals that affect contractility are called inotropic agents. For example drugs such as catecholamines (norepinephrine and epinephrine) that enhance contractility are considered to have a positive inotropic effect. All factors that cause an increase in contractility work by causing an increase in intracellular calcium concentration [Ca++] during contraction.

The concept of contractility was necessary to explain why some interventions (e.g. an adrenaline infusion) could cause an increase in myocardial performance even if, as could be shown in experiments, the preload, afterload and heart rate were all held constant. Experimental work controlling the other factors was necessary because a change in contractility is generally not an isolated effect. For example, an increase in sympathetic stimulation to the heart increases contractility and heart rate. An increase in contractility tends to increase stroke volume and thus a secondary decrease in preload.

Blood pressure is the pressure exerted by the blood on the walls of the blood vessels. Unless indicated otherwise, blood pressure refers to systemic arterial blood pressure, i.e., the pressure in the large arteries delivering blood to body parts other than the lungs, such as the brachial artery (in the arm). The pressure of the blood in other vessels is lower than the arterial pressure. Blood pressure values are universally stated in millimeters of mercury (mm Hg), and are always given relative to atmospheric pressure. For example, the absolute pressure of the blood in an artery with mean arterial pressure stated as 100 mm Hg, on a day with atmospheric pressure of 760 mm Hg, is 860 mm Hg.

The systolic pressure is defined as the peak pressure in the arteries during the cardiac cycle; the diastolic pressure is the lowest pressure (at the resting phase of the cardiac cycle). The mean arterial pressure and pulse pressure are other important quantities. Typical values for a resting, healthy adult are approximately 120 mm Hg systolic and 80 mm Hg diastolic (written as 120/80 mm Hg), with large individual variations. These measures of blood pressure are not static, but undergo natural variations from one heartbeat to another or throughout the day (in a circadian rhythm); they also change in response to stress, nutritional factors, drugs, or disease.

An instance of the connection between the vagus nerve and blood pressure regulation may be found in U.S. Pat. No. 5,707,400 ("'400"), to Terry, et al., titled, "Treating refractory hypertension by nerve stimulation," which is incorporated in its entirety by reference. Hypertension (higher than normal blood pressure) and its converse, hypotension (lower than normal blood pressure), largely comprise the two sides of the coin that represents the problems relating to blood pressure. Issuing relating to hypotension, its causes and effects, are discussed also in U.S. Patent Application No. 20050283197 A1, to Daum, et al., titled, "Systems and methods for hypotension," which is incorporated in its entirety by reference.

Blood pressure exceeding normal values is called arterial hypertension. It itself is only rarely an acute problem, with the seldom exception of hypertensive crisis, such as severe hypertension with acute impairment of an organ system (especially the central nervous system, cardiovascular system and/or the renal system) and the possibility of irreversible organ-damage. However, because of its long-term indirect effects (and also as an indicator of other problems) it is a serious worry to physicians diagnosing it. Persistent hypertension is one of the risk factors for strokes, heart attacks, heart failure, arterial aneurysms, and is the second leading cause of chronic renal failure after diabetes mellitus.

All level of blood pressure puts mechanical stress on the arterial walls. Higher pressures increase heart workload and progression of unhealthy tissue growth (atheroma) that develops within the walls of arteries. The higher the pressure, the more stress that is present and the more atheroma tend to progress and the heart muscle tends to thicken, enlarge and become weaker over time.

Blood pressure that is too low is known as hypotension. Low blood pressure may be a sign of severe disease and requires more urgent medical attention. When blood pressure and blood flow is very low, the perfusion of the brain may be critically decreased (i.e., the blood supply is not sufficient), causing lightheadedness, dizziness, weakness and fainting.

Sometimes the blood pressure drops significantly when a patient stands up from sitting. This is known as orthostatic hypotension; gravity reduces the rate of blood return from the body veins below the heart back to the heart, thus reducing stroke volume and cardiac output. When people are healthy, they quickly constrict the veins below the heart and increase their heart rate to minimize and compensate for the gravity effect. This is done at a subconscious level via the autonomic nervous system. The system usually requires a few seconds to fully adjust and if the compensations are too slow or inadequate, the individual will suffer reduced blood flow to the brain, dizziness and potential blackout. Increases in G-loading, such as routinely experienced by supersonic jet pilots "pulling Gs", greatly increases this effect. Repositioning the body perpendicular to gravity largely eliminates the problem.

Hypotension often accompanies and complicates many other systemic health problems, such as anaphylaxis and sepsis, leading to anaphylactic shock and septic shock, making it more difficult to address the underlying health problem. For example, U.S. Patent Application No. 20050065553, Ben Ezra, et al., titled, "Applications of vagal stimulation," which is incorporated in its entirety by reference, proposes to a method to treat a patient's sepsis by applying an appropriately configured current to the vagus nerve. However, when accompanied with refractory arterial hypotension, sepsis becomes septic shock.

Septic shock is a serious medical condition causing such effects as multiple organ failure and death in response to infection and sepsis. Its most common victims are children and the elderly, as their immune systems cannot cope with the infection as well as those of full-grown adults, as well as immunocompromised individuals. The mortality rate from septic shock is approximately 50%. Other various shock conditions include: systemic inflammatory response syndrome, toxic shock syndrome, adrenal insufficiency, and anaphylaxis.

A subclass of distributive shock, shock refers specifically to decreased tissue perfusion resulting in end-organ dysfunction. Cytokines $TNF\alpha$, $IL-1\beta$, $IL-6$ released in a large scale inflammatory response may result in massive vasodilation, increased capillary permeability, decreased systemic vascular resistance, and hypotension. Hypotension reduces tissue perfusion pressure, and thus tissue hypoxia ensues. Finally, in an attempt to offset decreased blood pressure, ventricular dilatation and myocardial dysfunction will occur.

Accordingly, there is a need in the art for new products and methods for treating the immediate symptoms of anaphylaxis, anaphylactic shock, bronchial constriction, asthma, etc.

SUMMARY OF THE INVENTION

The present invention involves products and methods of treatment of anaphylaxis utilizing an electrical signal that may be applied to the vagus nerve to temporarily block and/or modulate the signals in the vagus nerve. The present invention also encompasses treatment of anaphylaxis, anaphylactic shock, bronchial constriction, asthma, etc.

In one or more embodiments, the present invention contemplates methods and apparatus for delivering one or more electrical impulses to at least one selected region of the vagus nerve to block and/or modulate signals to the muscle fibers of the heart facilitating contractility, the fibers surrounding the cardiac tissue facilitating an increase in heart function (thereby raising blood pressure), and/or the muscle fibers surrounding the bronchi (facilitating opening of airways).

It shall be understood that the activation of such impulses may be directed manually by a patient suffering from anaphylaxis.

In one or more embodiments of the present invention, the impulses are applied in a manner that relaxes the myocardium to reduce the baseline level of tonic contraction, effects vasoconstriction (or dilation), and in cases of some shock, relaxes the smooth muscle lining the bronchial passages to relieve the spasms that occur, such as during anaphylactic shock. The impulses may be applied by positioning leads on the nerves that control cardiac activity, and/or bronchial activity respectively, such as the superior and/or inferior cardiac branches, and/or the anterior and/or posterior bronchial branches, of the right and/or left branches of the vagus nerve, which join with fibers from the sympathetic nerve chain to form the anterior and posterior coronary and pulmonary plexuses. Leads may be positioned above one or both of the cardiac and pulmonary branches of the vagus nerve to include a block and/or modulation of both organs. It shall also be understood that leadless impulses as shown in the art may also be utilized for applying impulses to the target regions.

The mechanisms by which the appropriate impulse is applied to the selected region of the vagus nerve can include positioning the distal ends of an electrical lead or leads in the vicinity of the nervous tissue controlling the myocardium, vessels of the heart (e.g., to affect vasoconstriction/dilation) and/or pulmonary muscles, which leads are coupled to an implantable or external electrical impulse generating device. The electric field generated at the distal tip of the lead creates a field of effect that permeates the target nerve fibers and causes the blocking and/or modulating of signals to the subject muscles.

The application of electrical impulses, either to the vagus nerve or the fibers branching off the vagus nerve to the cardiac muscles and/or the bronchial muscles to modulate the parasympathetic tone in order to relax the body's reaction to anaphylaxis is more completely described in the following detailed description of the invention, with reference to the drawings provided herewith, and in claims appended hereto.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims of an issued utility application.

DETAILED DESCRIPTION OF THE PREFERRED EMBODIMENT

It shall be understood that the embodiments disclosed herein are representative of preferred aspects of the invention and are so provided as examples of the invention. The scope of the invention, however, shall not be limited to the disclosures provided herein, nor by the provisional claims appended hereto.

While the exact physiological causes of anaphylaxis (e.g., inducing bronchial constriction and/or hypotension) have not been determined, the present invention postulates that the direct mediation of the smooth muscle constriction is the result of over-activity in the vagus nerve, which is a response to the flood of pro-inflammatory mediators' interacting with the receptors on the nerve fibers themselves.

It has been observed in the literature that the nervous system maintains a balance of the signals carried by the sympathetic and parasympathetic nerves. The vagus nerve, as the source of the signal to constrict bronchial smooth muscle and/or the cardiac muscle, is thought to provide a baseline level of tonicity in the smooth muscles surrounding the bronchial passages and cardiac muscle, in order to: (i) prevent the tissue lining the airways from collapsing shut; and/or (ii) to prevent tissue from expanding too much and depressing blood pressure.

Specifically, one or more embodiments of the present invention consider the signals carried by the vagus (parasympathetic) nerve to cause: (i) a constriction of the smooth muscle surrounding the bronchial passages, and/or (ii) a slowing of the heart. The sympathetic nerve fibers carry the opposing signals that tend to open the bronchial passages as well as speed up the heart rate. It should be recognized that the signals of the vagus nerve mediate a response similar to that of histamine, while the sympathetic signals generate an effect similar to epinephrine. Given the postulated balance between the parasympathetic and sympathetic signals, removing the parasympathetic signal should create an imbalance emphasizing the sympathetic signal. Along these lines, scientific literature also indicates that severing the vagus nerve in dogs will raise the animals' heart rates, as well as open the bronchial passages, much the same way that epinephrine does.

Figure 1:
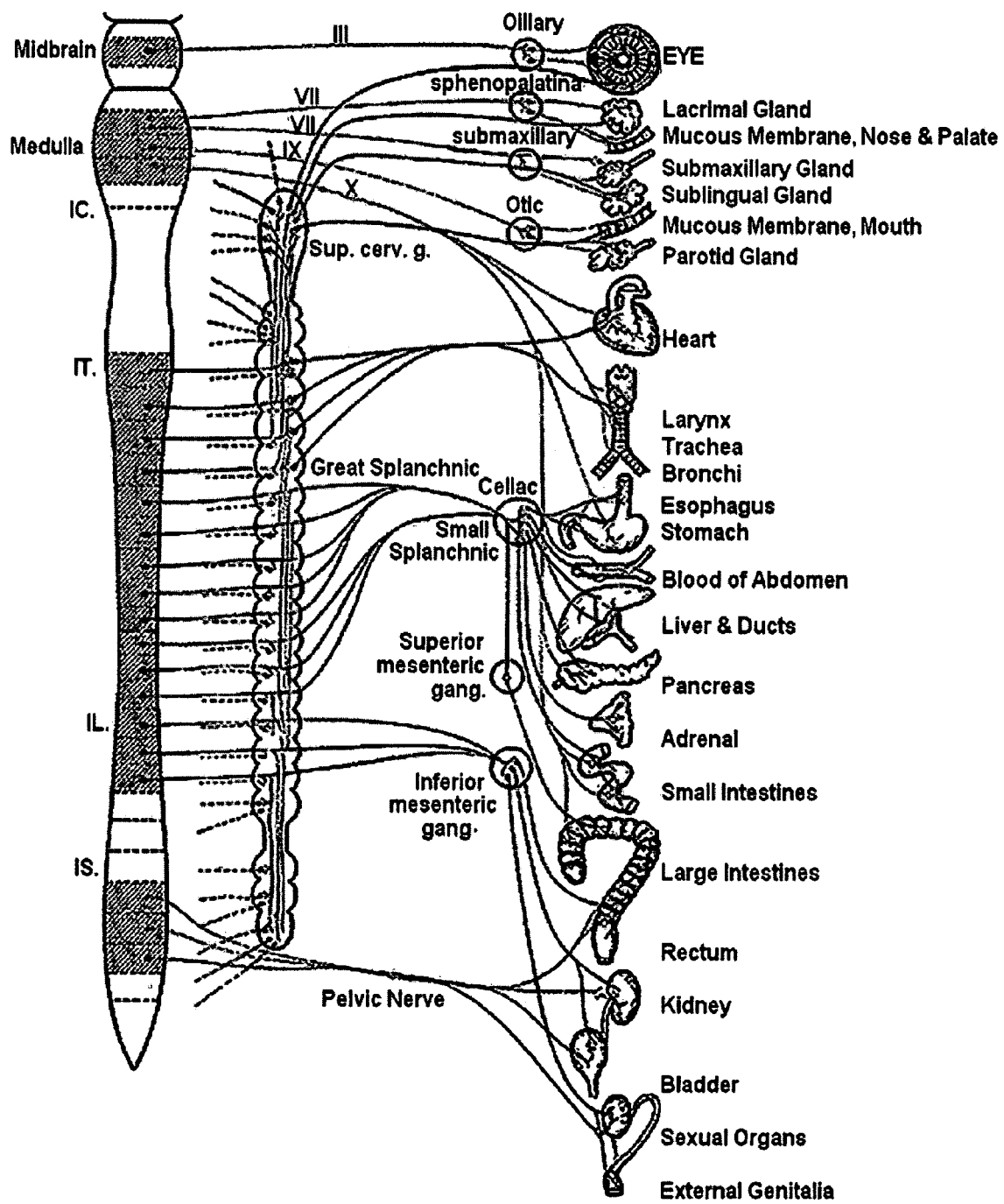
FIG. 1 is a diagrammatic view of the sympathetic and parasympathetic nerve systems.
Figure 2:
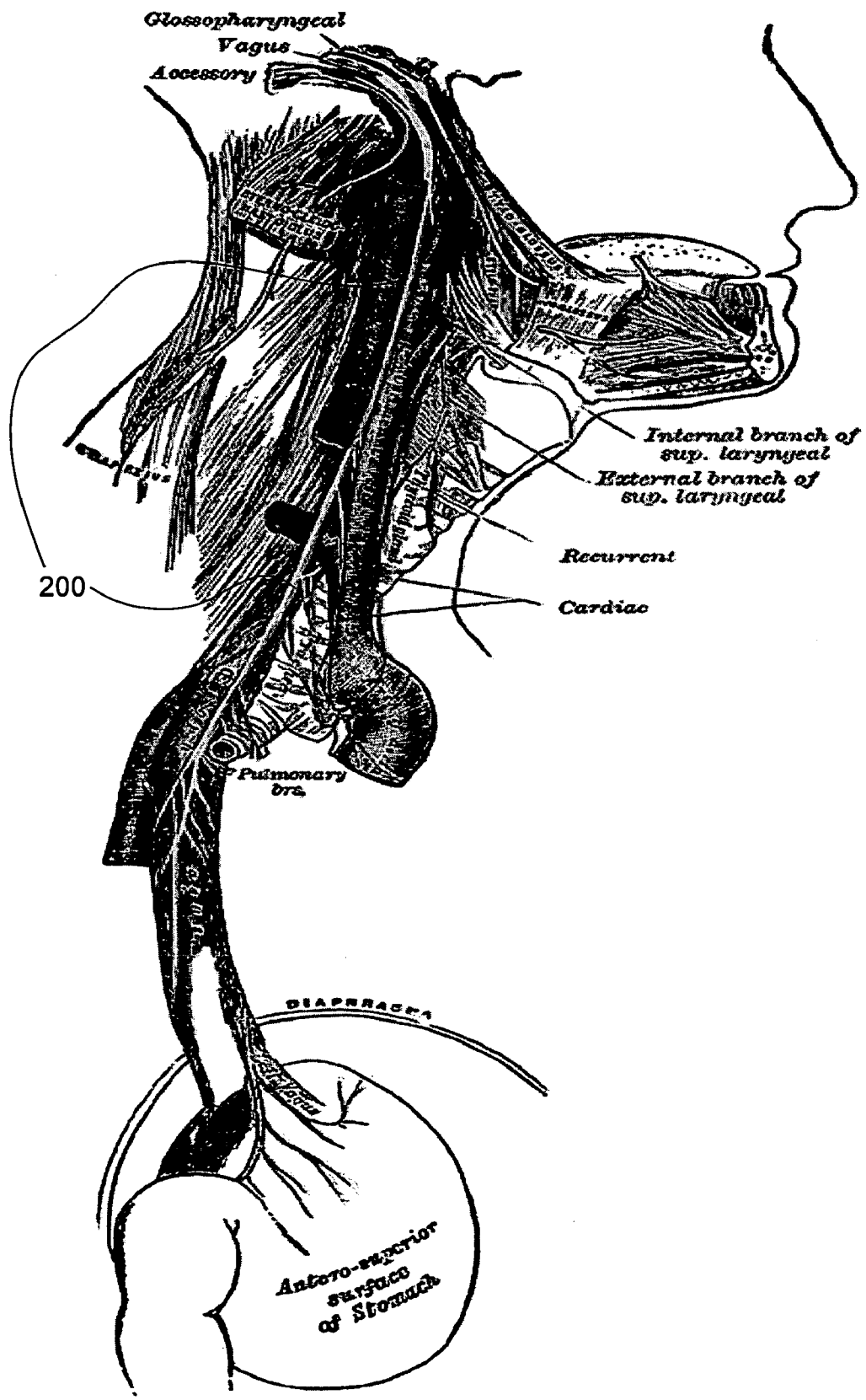
FIG. 2 is a cross-sectional anatomical illustration of selected portions of a neck, thoracic and abdominal region.

Now referring to FIGS. 1 and 2, the vagus nerve is shown in more detail. The vagus nerve is composed of motor and sensory fibers. The vagus nerve leaves the cranium and is contained in the same sheath of dura matter with the accessory nerve. The vagus nerve passes down the neck within the carotid sheath to the root of the neck. The branches of distribution of the vagus nerve include, among others, the superior cardiac, the inferior cardiac, the anterior bronchial and the posterior bronchial branches. On the right side, the vagus nerve descends by the trachea to the back of the root of the lung, where it spreads out in the posterior pulmonary plexus. On the left side, the vagus nerve enters the thorax, crosses the left side of the arch of the aorta, and descends behind the root of the left lung, forming the posterior pulmonary plexus.

In mammals, two vagal components have evolved in the brainstem to regulate peripheral parasympathetic functions. The dorsal vagal complex (DVC), consisting of the dorsal motor nucleus (DMNX) and its connections, controls parasympathetic function below the level of the diaphragm, while the ventral vagal complex (VVC), comprised of nucleus ambiguus and nucleus retrofacial, controls functions above the diaphragm in organs such as the heart, thymus and lungs, as well as other glands and tissues of the neck and upper chest, and specialized muscles such as those of the esophageal complex.

The parasympathetic portion of the vagus innervates ganglionic neurons which are located in or adjacent to each target organ. The VVC appears only in mammals and is associated with positive as well as negative regulation of heart rate, bronchial constriction, vocalization and contraction of the facial muscles in relation to emotional states. Generally speaking, this portion of the vagus nerve regulates parasympathetic tone. The VVC inhibition is released (turned off) in states of alertness. This in turn causes cardiac vagal tone to decrease and airways to open, to support responses to environmental challenges.

The parasympathetic tone is balanced in part by sympathetic innervation, which generally speaking supplies signals tending to expand the myocardium, affect vasoconstriction, and/or to relax the bronchial muscles, so that over-contraction and over-constriction, respectively, do not occur. Overall, myocardium tone, vasodilation, and/or airway smooth muscle tone are dependent on several factors, including parasympathetic input, inhibitory influence of circulating epinephrine, NANC inhibitory nerves and sympathetic innervation of the parasympathetic ganglia. Stimulation of the vagus nerve (up-regulation of tone), such as may occur in shock, results in a heart rate decrease and airway constriction. In this context, up-regulation is the process by which the specific effect is increased, whereas down-regulation involves a decrease of the effect. In general, the pathology of shock appears to be mediated by inflammatory cytokines that overwhelm receptors on the nerve cells and cause the cells to massively up-regulate the parasympathetic tone. On a cellular level, up-regulation is the process by which a cell increases the number of receptors to a given hormone or neurotransmitter to improve its sensitivity to this molecule. A decrease of receptors is called down-regulation.

Anaphylaxis appears to be mediated predominantly by the hypersensitivity to an allergen causing the massive overproduction of cholenergic receptor activating cytokines that overdrive the otherwise normally operating vagus nerve to signal massive constriction of the airways.

In the case of asthma (which may be related to anaphylaxis), it appears that the airway tissue has both (i) a hypersensitivity to the allergen that causes the overproduction of the cytokines that stimulate the cholenergic receptors of the nerves and/or (ii) a baseline high parasympathetic tone or a high ramp up to a strong parasympathetic tone when confronted with any level of cholenergic cytokine. The combination can be lethal.

Sepsis is mediated by severe infection and may result in a large scale inflammatory response that releases cytokines TNFα, IL-1β, IL-6 mediating massive vasodilation, increased capillary permeability, decreased systemic vascular resistance, and hypotension. By comparison, anaphylaxis appears to be mediated predominantly by the hypersensitivity to an allergen causing the massive overproduction of cholenergic receptor activating cytokines that overdrive the otherwise normally operating vagus nerve to signal massive constriction of the airways. Drugs such as epinephrine drive heart rate up while also relaxing the bronchial muscles, effecting temporary relief of symptoms from these conditions.

Drugs such as epinephrine drive heart rate up while also relaxing the bronchial muscles, effecting temporary relief of symptoms from these conditions. As mentioned above, experience has shown that severing the vagus nerve (an extreme version of reducing the parasympathetic tone) has an effect similar to that of epinephrine and adrenaline on heart rate and bronchial diameter in that the heart begins to race (tachycardia) and the bronchial passageways dilate.

In accordance with at least one aspect of the present invention, the delivery, in a patient suffering from anaphylaxis, anaphylactic shock, bronchial constriction, asthma, etc., an electrical impulse sufficient to block and/or modulate transmission of signals along the vagus nerve will result in relaxation of the bronchi smooth muscle, dilating airways, raising the heart function (and thus the blood pressure), and/or counteract the effect of anaphylaxis and/or histamine on the vagus nerve. Depending on the placement of the impulse, the signal blocking and/or modulation can also raise the heart function.

In accordance with at least one aspect of the present invention, blocking and/or modulating the signal in the vagus nerve, and/or blocking and/or affecting the anaphylaxis or histamine response of the vagus nerve, to reduce parasympathetic tone provides an immediate emergency response, much like a defibrillator, in situations of anaphylaxis, anaphylactic shock, bronchial constriction, asthma, etc., providing immediate temporary dilation of the airways and/or an increase of heart function until subsequent measures, such as administration of medication, rescue breathing and intubation can be employed. Moreover, the teachings of the present invention permit immediate airway dilation and/or heart function increase to enable subsequent life saving measures that otherwise would be ineffective or impossible due to severe constriction or other physiological effects. Treatment in accordance with the present invention provides bronchodilation and/or increased heart function for a long enough period of time so that administered medication (such as epinephrine) has time to take effect before the patient suffocates.

The methods described herein of applying an electrical impulse to a selected region of the vagus nerve may further be refined such that the at least one region may comprise at least one nerve fiber emanating from the patient's tenth cranial nerve (the vagus nerve), and in particular, at least one of the anterior bronchial branches thereof, at least one of the posterior bronchial branches thereof, at least one of the superior cardiac branches thereof, and/or at least one of the inferior cardiac branches thereof. Preferably the impulse is provided to at least one of the anterior pulmonary or posterior pulmonary plexuses aligned along the exterior of the lung. As necessary, the impulse may be directed to nerves innervating only the bronchial tree and lung tissue itself. In addition, the impulse may be directed to a region of the vagus nerve to block and/or modulate one or both of the cardiac and bronchial branches. As recognized by those having skill in the art, this embodiment should be carefully evaluated prior to use in patients known to have preexisting cardiac issues.

With respect to the cardiac branches, the cardiac plexus is situated at the base of the heart, and is divided into a superficial part, which lies in the concavity of the aortic arch, and a deep part, between the aortic arch and the trachea. The two parts are, however, closely connected. The superficial part of the cardiac plexus lies beneath the arch of the aorta, in front of the right pulmonary artery. It is formed by the superior cardiac branch of the left sympathetic nerve and the lower superior cervical cardiac branch of the left vagus. The superficial part of the cardiac plexus gives branches (a) to the deep part of the plexus; (b) to the anterior coronary plexus; and (c) to the left anterior pulmonary plexus. The deep part of the cardiac plexus is situated in front of the bifurcation of the trachea, above the point of division of the pulmonary artery, and behind the aortic arch. It is formed by the cardiac nerves derived from the cervical ganglia of the sympathetic, and the cardiac branches of the vagus and recurrent nerves. The only cardiac nerves which do not enter into the formation of the deep part of the cardiac plexus are the superior cardiac nerve of the left sympathetic nerve, and the lower of the two superior cervical cardiac branches from the left vagus, which pass to the superficial part of the plexus.

Figure 3:
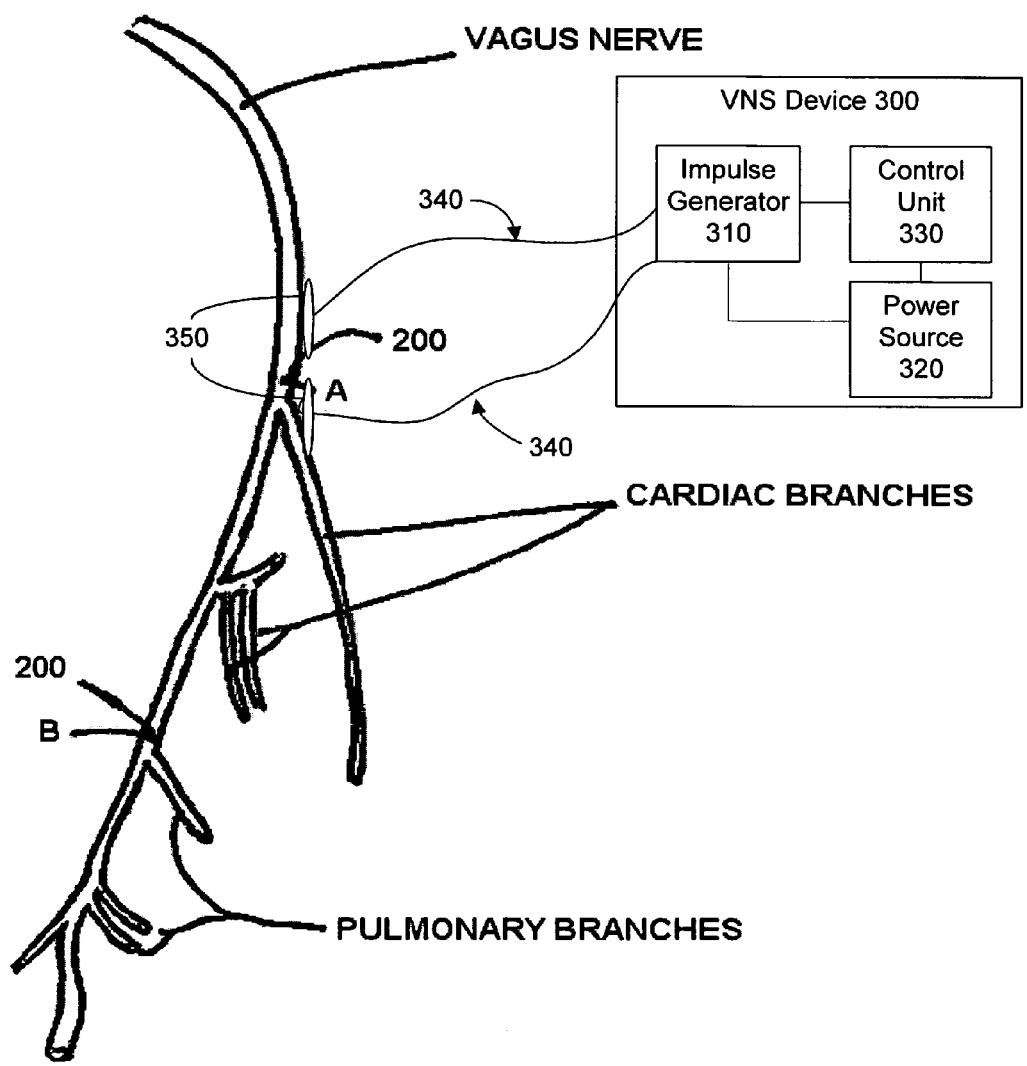
FIG. 3 illustrates a simplified view of the vagus nerve shown in FIGS. 1 and 2.

Further reference is now made to FIG. 3, which illustrates a simplified view of the vagus nerve shown in FIG. 2 and cardiac and pulmonary branches thereof. Also shown is a vagus nerve stimulation (VNS) device 300 for stimulation of the vagus nerve. VNS device 300 is intended for the treatment of anaphylaxis, anaphylactic shock, bronchial constriction, asthma, hypotension, etc. VNS device 300 may include an electrical impulse generator 310; a power source 320 coupled to the electrical impulse generator 310; a control unit 330 in communication with the electrical impulse generator 310 and coupled to the power source 320; and electrodes 340 coupled to the electrical impulse generator 310 for attachment via leads 350 to one or more selected regions 200A, 200B of a vagus nerve 200 of a mammal. The control unit 330 may control the electrical impulse generator 310 for generation of a signal suitable for amelioration of, for example, the bronchial constriction or hypotension when the signal is applied via the electrodes 340 to the vagus nerve 200. It is noted that VNS device 300 may be referred to by its function as a pulse generator.

In accordance with one embodiment, one or more electrical impulses are directed to location A on or near the vagus nerve above the cardiac branch. In this embodiment one or more electrical impulses are introduced at the location A to block and/or modulate and/or inhibit up-regulation of the parasympathetic tone and effect a dilation of airways and increase in heart function.

In accordance with another embodiment, one or more electrical impulses are directed to location B on or near the vagus nerve below the cardiac branch proximal to the pulmonary branch. In this embodiment one or more electrical impulses are introduced at the location B to block and/or modulate and/or inhibit up-regulation of the parasympathetic tone to effect only a dilation of airways.

In patients known to be subject to anaphylactic shock or severe asthma attacks, one or more electrical impulse emitting devices 300 may be implanted in one or more selected regions 200A, 200B of the vagus nerve 200. Device 300 may be percutaneous for emergency applications, wherein device 300 may comprise an electrode 340 powered via an external power source 320.

U.S. Patent Application Publications 2005/0075701 and 2005/0075702, both to Shafer, both of which are incorporated herein by reference, relating to stimulation of neurons of the sympathetic nervous system to attenuate an immune response, contain descriptions of pulse generators that may be applicable to the present invention.

Figure 4:
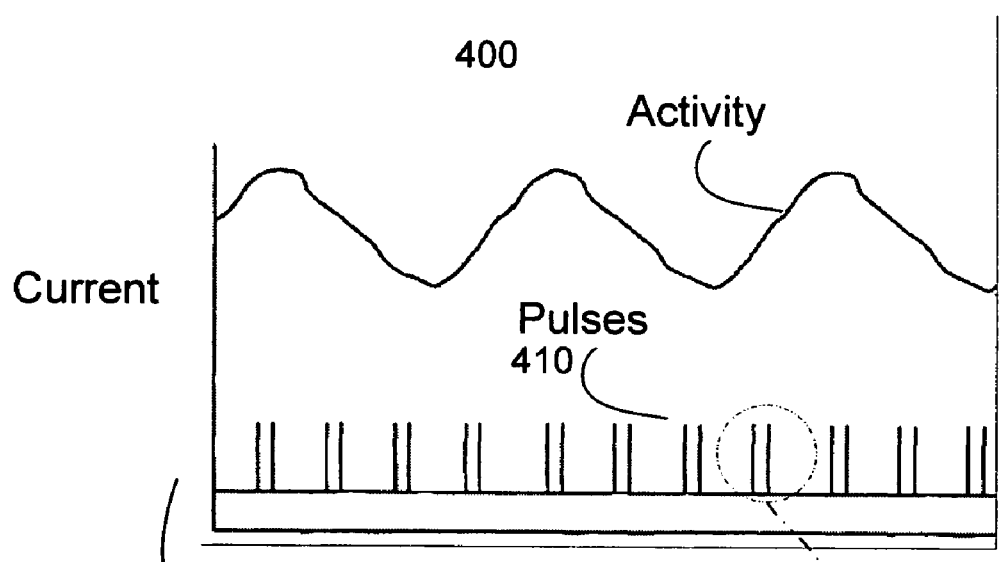
FIG. 4 illustrates an exemplary electrical voltage/current profile for a blocking and/or modulating impulse applied to a portion or portions of the vagus nerve in accordance with an embodiment of the present invention.
Figure 4:
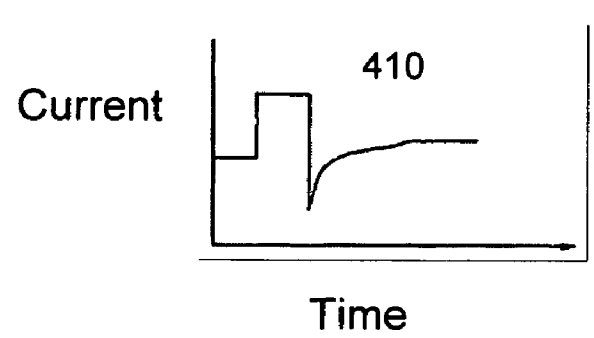

FIG. 4 illustrates an exemplary electrical voltage/current profile for a blocking and/or modulating impulse applied to a portion or portions of the vagus nerve in accordance with an embodiment of the present invention. A suitable electrical voltage/current profile 400 for the blocking and/or modulating impulse 410 to the portion or portions 200A, 200B of the vagus nerve 200 may be achieved using a pulse generator 310. In a preferred embodiment, the pulse generator 310 may be implemented using a power source 320 and a control unit 330 having, for instance, a processor, a clock, a memory, etc., to produce a pulse train 420 to the electrode(s) 340 that deliver the blocking and/or modulating impulse 410 to the nerve 200 via leads 350. For percutaneous use, the VNS device 300 may be available to the surgeon as external emergency equipment. For subcutaneous use, the VNS device 300 may be surgically implanted, such as in a subcutaneous pocket of the abdomen. The VNS device 300 may be powered and/or recharged from outside the body or may have its own power source 320. By way of example, the VNS device 300 may be purchased commercially. The VNS device 300 is preferably programmed with a physician programmer, such as a Model 7432 also available from Medtronic, Inc.

The parameters of the modulation signal 400 are preferably programmable, such as the frequency, amplitude, duty cycle, pulse width, pulse shape, etc. In the case of an implanted pulse generator, programming may take place before or after implantation. For example, an implanted pulse generator may have an external device for communication of settings to the generator. An external communication device may modify the pulse generator programming to improve treatment.

The electrical leads 350 and electrodes 340 are preferably selected to achieve respective impedances permitting a peak pulse voltage in the range from about 0.2 volts to about 20 volts.

The blocking and/or modulating impulse signal 410 preferably has a frequency, an amplitude, a duty cycle, a pulse width, a pulse shape, etc. selected to influence the therapeutic result, namely blocking and/or modulating some or all of the vagus nerve transmissions. For example the frequency may be about 1 Hz or greater, such as between about 25 Hz to 3000 Hz, or between about 1000 Hz to about 2500 Hz. (These are notably higher frequencies than typical nerve stimulation or modulation frequencies.) The modulation signal may have a pulse width selected to influence the therapeutic result, such as about 20 µS or greater, such as about 20 µS to about 1000 µS. The modulation signal may have a peak voltage amplitude selected to influence the therapeutic result, such as about 0.2 volts or greater, such as about 0.2 volts to about 20 volts.

In accordance with a preferred embodiment, VNS devices 300 in accordance with the present invention are provided in the form of a percutaneous or subcutaneous implant that can be reused by an individual.

In accordance with another embodiment, devices in accordance with the present invention are provided in a "pacemaker" type form, in which electrical impulses 410 are generated to a selected region 200A, 200B of the vagus nerve 200 by VNS device 300 on an intermittent basis to create in the patient a lower reactivity of the vagus nerve 200 to up-regulation signals.

In accordance with another embodiment, devices 300 in accordance with the present invention are incorporated in an endotracheal tube device to ameliorate bronchospasm during surgery. In a preferred embodiment one or more devices 300 are located in the distal portion of an endotracheal tube to contact selected regions 200A, 200B of the vagus nerve 200 to impart appropriate electrical impulses to dampen reactivity of the vagus nerve 200 to stimulus. In all cases of permanent implantation, however, the implanting surgeon should vary the signal modulated by the control unit 330 and specific location of the lead 350 until the desired outcome is achieved, and should monitor the long-term maintenance of this effect to ensure that adaptive mechanisms in the patient's body do not nullify the intended effects.

In addition, or as an alternative to the devices to implement the modulation unit for producing the electrical voltage/current profile of the blocking and/or modulating impulse to the electrodes, the device disclosed in U.S. Patent Publication No.: 2005/0216062 (the entire disclosure of which is incorporated herein by reference), may be employed. U.S. Patent Publication No.: 2005/0216062 discloses a multi-functional electrical stimulation (ES) system adapted to yield output signals for effecting faradic, electromagnetic or other forms of electrical stimulation for a broad spectrum of different biological and biomedical applications. The system includes an ES signal stage having a selector coupled to a plurality of different signal generators, each producing a signal having a distinct shape such as a sine, a square or a saw-tooth wave, or simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

Prior to discussing experimental results, a general approach to treating anaphylaxis, anaphylactic shock, bronchial constriction, asthma, hypotension, etc., in accordance with one or more embodiments of the invention may include applying at least one electrical impulse to one or more selected regions of the vagus nerve of a mammal in need of relief from anaphylaxis.

The method may include: implanting one or more electrodes to the selected regions of the vagus nerve; and applying one or more electrical stimulation signals to the electrodes to produce the at least one electrical impulse, wherein the one or more electrical stimulation signals are of a frequency between about 1 Hz to 3000 Hz, and an amplitude of between about 1-6 volts.

The one or more electrical stimulation signals may be of a frequency between about 750 Hz to 1250 Hz; or between about 10 Hz to 35 Hz. The one or more electrical stimulation signals may be of an amplitude of between about 0.75 to 1.5 volts, such as about 1.25 volts. The one or more electrical stimulation signals may be one or more of a full or partial sinusoid, square wave, rectangular wave, and/or triangle wave. The one or more electrical stimulation signals may have a pulsed on-time of between about 50 to 500 microseconds, such as about 100, 200 or 400 microseconds.

The polarity of the pulses may be maintained either positive or negative. Alternatively, the polarity of the pulses may be positive for some periods of the wave and negative for some other periods of the wave. By way of example, the polarity of the pulses may be altered about every second.

While up-regulating the signal provided by the sympathetic nerves may accomplish the desired treatment effect, the present invention suggests that a more direct route to immediately breaking the cycle of anaphylaxis, anaphylactic shock, bronchial constriction, asthma, hypotension, etc., is via the vagus nerve because the mode of action for the hypersensitivity response is at the vagus nerve and not through the sympathetic nerves. Therefore, experiments were performed to identify exemplary methods of how electrical signals can be supplied to the peripheral nerve fibers that innervate and/or control the bronchial smooth muscle to (i) reduce the sensitivity of the muscle to the signals to constrict, and (ii) to blunt the intensity of, or break the constriction once it has been initiated. In addition, experiments were performed to identify exemplary methods of how electrical signals can be supplied to the peripheral nerve fibers that innervate and/or control vasoconstriction/dilation, and/or that innervate and/or control the myocardium to (i) reduce the sensitivity of the muscle to the signals of tonic contraction, and (ii) to blunt the intensity of, or break the tonic over-contraction once it has been initiated.

In particular, specific signals, selected from within a range of known nerve signals, were applied to the vagus nerves and/or the sympathetic nerves in guinea pigs, to produce selective interruption or reduction in the effects of lung vagal nerve activity leading to attenuation of anaphylaxis-induced bronchoconstriction and/or hypotension.

Experimentation

As opposed to experiments in which hypotension and/or bronchial constriction is induced using i.v. histamine, the testing procedure and test data below were obtained in response to anaphylaxis. Fifteen male guinea pigs (400 g) were sensitized by the intraperitoneal injection of ovalbumin (10 mg/kg i.p. every 48 hrs for three doses). Three weeks later animals were transported to the lab and immediately anesthetized with an i.p. injection of urethane 1.5 g/kg. Skin over the anterior neck was opened and the carotid artery and both jugular veins were cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyzed chest wall musculature to remove the contribution of chest wall rigidity from airway pressure measurements. Both vagus nerves were isolated and connected to shielded electrodes to allow selective stimuli of these nerves in the manner disclosed in the one or more embodiments disclosed above. Following fifteen minutes of stabilization, baseline hemodynamic and airway pressure measurements were made before and after the administration of increasing concentrations of ovalbumin (0.001-1.0 mg/kg i.v.). Following the increase in airway pressure and hypotension accompanying the anaphylactic response, vagal nerve modulation was made at variations of frequency, voltage and pulse duration to identity parameters that attenuate the hypotensive and bronchoconstrictive responses. Euthanasia was accomplished with intravenous potassium chloride.

Figure 5:
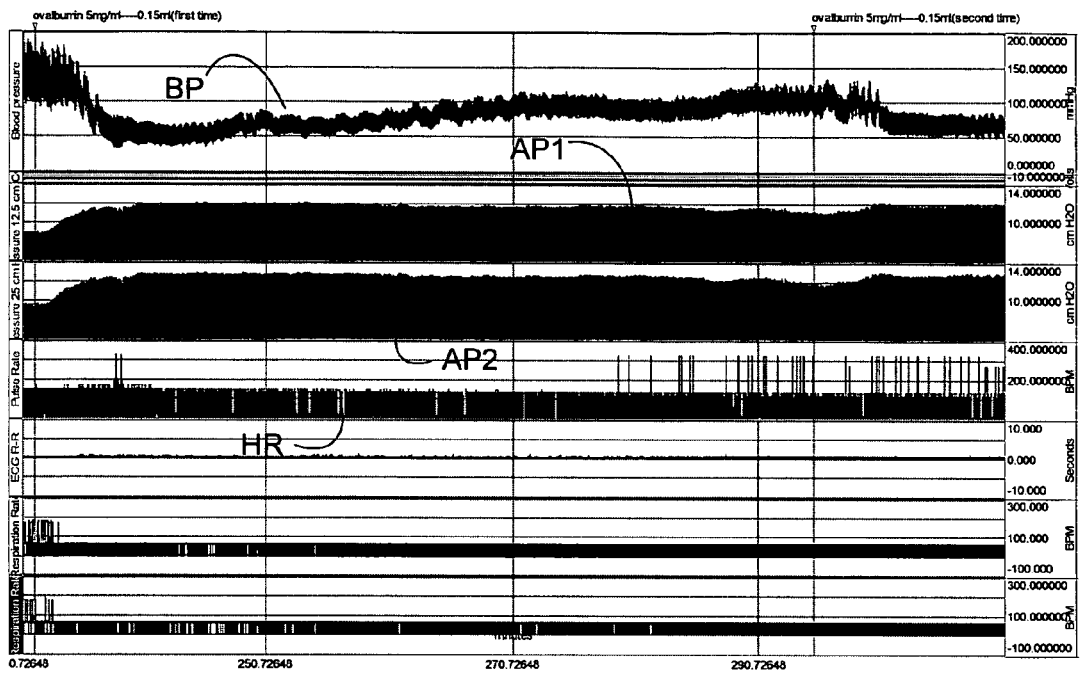
FIGS. 5-7 graphically illustrate experimental data obtained in accordance with multiple embodiments of the present invention.

With reference to FIG. 5, the top line (BP) shows blood pressure, the second line shows airway pressure (AP1), the third line shows airway pressure (AP2) on another sensor, the fourth line is the heart rate (HR) derived from the pulses in the blood pressure. As a baseline of the anaphylactic reaction that is achieved in this model, the first guinea pig's response to the ovalbumin was recorded without any electrical stimulation. The graph in FIG. 20 shows the effect of an injection of 0.75 mg of ovalbumin. About five minutes after the injection, the blood pressure dropped from 125 to 50 mmHg while the airway pressure increased from 11 to 14 cm $H_2O$. This effect was sustained for over sixty (60) minutes with the blood pressure showing some recovery to 90 mmHg.

Figure 6:
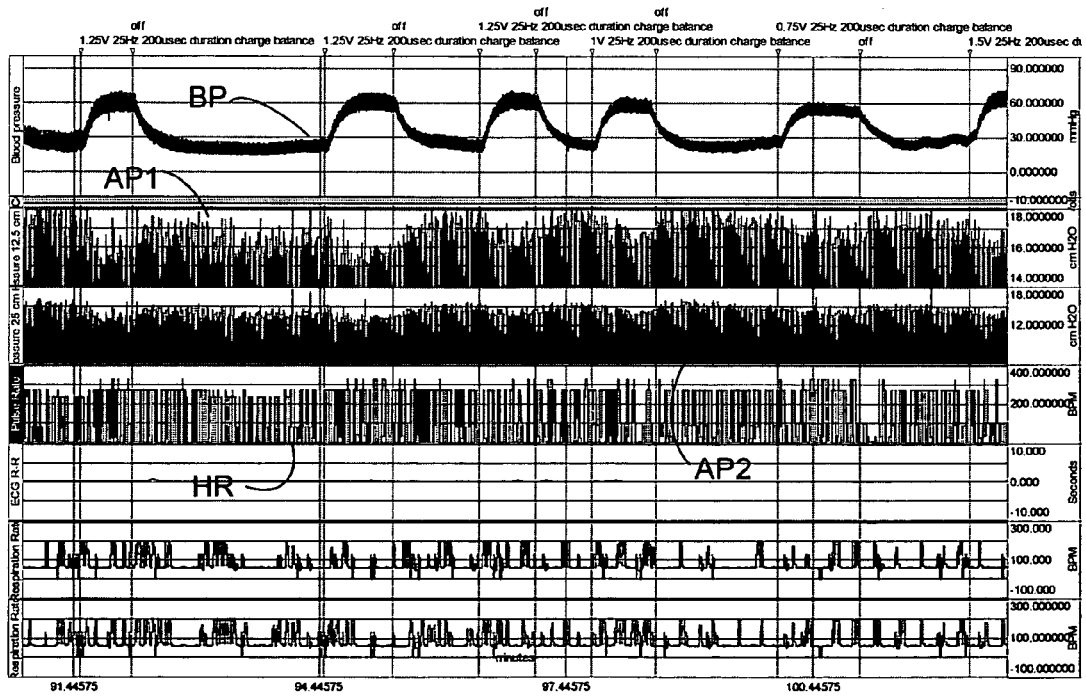

With reference to FIG. 6, another animal (guinea pig #2) was tested to determine the effect of the signals that were shown to be effective in the histamine induced asthma model (Experimental Procedure 1 above). FIG. 21 demonstrates the effect of a 25 Hz, 200 uS, 1.25V square wave signal applied simultaneously to both left and right vagus nerves in sensitized guinea pig #2 after injection with 1.125 mg ovalbumin to cause an anaphylactic response. The larger dose was used to cause a more severe reaction. Starting from the left side of the graph, it may be seen that before electrical stimulation, the blood pressure was severely depressed at 30 mmHg while the airway pressure was almost 22 cm $H_2O$ (9.5 cm increase over baseline). The first peak in blood pressure coincides with the electrical signal applied to the vagus—the blood pressure increased to 60 mmHg (a 100% increase) while the airway pressure reduced by 6.5 cm to about 15.5 cm $H_2O$ (a 68% reduction). The next peak shows the effect repeated. The other peaks show the effects of changing the signal voltage—lowering the voltage results in reduced effectiveness.

Figure 7:
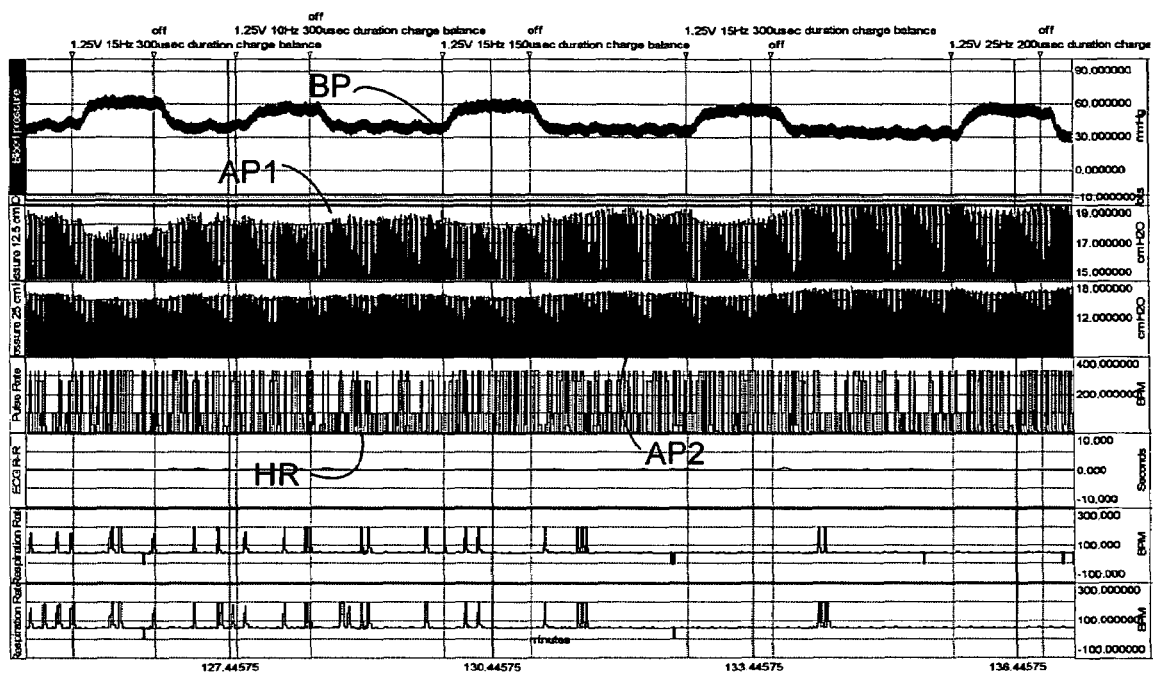

With reference to FIG. 7, the effect of changing the signal frequency and pulse width on blood pressure and airway pressure is shown. The first peak in blood pressure coincides with a 15 Hz, 300 uS, 1.25V electrical signal applied to both sides of the vagus—the blood pressure was increased to 60 mmHg (a 70% increase) while the airway pressure was reduced by 1.5 cm to about 17 cm $H_2O$ (a 25% reduction). The next peak demonstrates a 10 Hz signal—the beneficial effects are reduced compared to 15 Hz. The other peaks show the effects of changing the signal frequency and pulse width—lowering the frequency below 15 Hz or lowering the pulse width below 200 uS results in reduced effectiveness. The signals between 15-25 Hz, and 200-300 uS maintain about the same effectiveness in decreasing the hypotensive and bronchoconstrictive symptoms of anaphylaxis.

Conclusions that may be drawn from the above experimental data include: (1) That the airway constriction and hypotension caused by anaphylaxis in guinea pigs can be significantly reduced by applying appropriate electrical signals to the vagus nerve. (2) That signals from 15 Hz to 25 Hz, 200 uS to 300 uS, and 1.0V to 1.5V were equally effective. (3) That a 25 Hz, 200 µS, 1.25V signal applied to the vagus nerve, airway constriction due to anaphylaxis was reduced up to 68%. This effect has been repeated on several animals. (4) That the 25 Hz, 200 uS, 1.25V signal applied to the vagus nerve produces up to a 100% increase in blood pressure in an anaphylactic guinea pig experiencing severe hypotension. This effect has been repeated on several animals. This may have applications in the treatment of other low blood pressure conditions such as septic shock. (5) That there is some evidence that the application of the signal to the vagus nerve may have the ability to shorten the duration of an anaphylactic episode.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating anaphylaxis, anaphylactic shock, bronchial constriction and/or asthma in a patient comprising applying at least one electrical impulse having a frequency between about 1 Hz and 3000 Hz to at least one selected nerve in a region of a parasympathetic nervous system of the patient, the electrical impulse being sufficient to increase a blood pressure and to relax bronchial smooth muscle and reduce a magnitude of constriction of the bronchial smooth muscle of the patient.

2. The method set forth in claim 1 wherein the region of the parasympathetic nervous system comprises a region of the vagus nerve proximal to at least one of the cardiac branch and the bronchial branch of the vagus nerve.

3. The method set forth in claim 2 wherein the region of the vagus nerve includes one or more of:
   the superior and/or inferior cardiac branches of the vagus nerve;
   the anterior and/or posterior bronchial branches of the vagus nerve;
   the right branch of the vagus nerve,
   the left branch of the vagus nerve;
   at or near the anterior or posterior coronary plexus; and
   at or near the anterior or posterior pulmonary plexus.

4. The method set forth in claim 1 wherein the electrical impulse does not substantially increase a heart rate of the patient.

5. The method of claim 1, wherein the electrical impulse has an amplitude of between about 1-10 volts.

6. The method of claim 5, wherein the electrical impulse has an amplitude of between about 1 volt to 2 volts.

7. The method of claim 1, wherein the electrical impulse has a pulsed-on time of between about 50 microseconds to about 800 microseconds.

8. The method of claim 1, wherein the electrical impulse has a pulsed-on time of about 200 microseconds to about 400 microseconds.

9. The method of claim 1, wherein the electrical impulse has a frequency of between about 10 to 50 Hz.

10. The method of claim 9, wherein the frequency is between about 15 to 30 Hz.

11. The method of claim 9, wherein the frequency is about 25 Hz.

12. A device for the treatment of anaphylaxis, anaphylactic shock, bronchial constriction and/or asthma in a patient comprising:
   an electrical impulse generator;
   a power source coupled to the electrical impulse generator;
   a control unit in communication with the electrical impulse generator and coupled to the power source;
   one or more electrodes coupled to the impulse pulse generator; and
   wherein the control unit is operable to modulate the electrical impulse generator for generation of a signal sufficient to elevate a blood pressure and relax bronchial smooth muscle and reduce a magnitude of constriction of the bronchial smooth muscle of the patient when the signal is applied via the one or more electrodes to a selected nerve in a region of the parasympathetic nervous system.

13. The device of claim 12, wherein the signal has a frequency of between about 1 to 3000 Hz.

14. The device of claim 13, wherein the frequency is between about 10 to 50 Hz.

15. The device of claim 12, wherein the signal has an amplitude of between about 1-10 volts.

16. The device of claim 12, wherein the signal has a pulsed-on time of between about 50 microseconds to about 800 microseconds.

17. The device of claim 12, wherein the signal has a pulsed-on time of about 200 microseconds to about 400 microseconds.

18. The device of claim 12 wherein the one or more electrodes are implantable within the patient.

19. A method of treating anaphylaxis, anaphylactic shock, bronchial constriction, and/or asthma in a patient, comprising applying at least one electrical impulse to one or more selected nerve(s) in one or more regions of the parasympathetic nervous system of the patient to increase a blood pressure and relax bronchial smooth muscle and reduce a magnitude of constriction of the bronchial smooth muscle of the patient.

20. The method of claim 19, further comprising:
   implanting one or more electrodes to the one or more regions of the parasympathetic nervous system; and
   applying one or more electrical stimulation signals to the electrodes to produce the at least one electrical impulse.

21. The method of claim 20, wherein the one or more electrical stimulation signals are of a frequency between about 1 Hz to 3000 Hz, and an amplitude of between about 1-12 volts.

22. The method of claim 21, wherein the one or more electrical stimulation signals are of a frequency between about 750 Hz to 1250 Hz.

23. The method of claim 21, wherein the one or more electrical stimulation signals are of a frequency between about 10 Hz to 35 Hz.

24. The method of claim 21, wherein the one or more electrical stimulation signals are of an amplitude of between about 0.75 to 1.5 volts.

25. The method of claim 21, wherein the one or more electrical stimulation signals are one or more of a full or partial sinusoid, square wave, rectangular wave, triangle wave.

26. The method of claim 21, wherein the one or more electrical stimulation signals have a pulsed on-time of between about 50 to 500 microseconds.

27. The method of claim 21, wherein the one or more electrical stimulation signals have a frequency of about 25 Hz, a pulsed on-time of about 200-400 microseconds, and an amplitude of about 1 volt.

28. The method of claim 21, wherein the one or more electrical stimulation signals have a frequency of about 25

Hz, a pulsed on-time of between about 100 to 400 microseconds, and an amplitude of about 1 volt.

29. The method of claim 28, wherein the pulsed on-time is one of: about 400 microseconds, about 200 microseconds, and about 100 microseconds.

30. The method of claim 21, further comprising maintaining a polarity of the pulse either positive or negative.

31. The method of claim 30, further comprising alternating the polarity of the pulse to be positive for some periods of the wave and negative for some other periods of the wave.

32. The method of claim 30, further comprising alternating the polarity of the pulse about every second.

* * * * *